United States Patent [19]

Geissler et al.

[11] Patent Number: 6,075,152
[45] Date of Patent: Jun. 13, 2000

[54] PROCESS FOR PREPARING ISOCHROMAN-3-ONES

[75] Inventors: Holger Geissler, Mainz; Ralf Pfirmann, Griesheim, both of Germany

[73] Assignee: Clariant GmbH, Frankfurt, Germany

[21] Appl. No.: 09/286,566

[22] Filed: Apr. 5, 1999

[30]   Foreign Application Priority Data

Apr. 6, 1998  [DE]  Germany ............................ 198 15 323

[51] Int. Cl.[7] .................................................. C07D 311/74
[52] U.S. Cl. ........................... 549/290; 549/289; 549/218
[58] Field of Search ..................... 549/218, 289, 549/290

[56]                References Cited

U.S. PATENT DOCUMENTS

| 5,231,194 | 7/1993 | Shirofuji et al. | 549/290 |
| 5,300,662 | 4/1994 | Nishida et al. | 549/290 |
| 5,886,211 | 3/1999 | Hirai et al. | 560/105 |

FOREIGN PATENT DOCUMENTS

| 0834497 | 4/1988 | European Pat. Off. . |
| WO 97/00850 | 1/1997 | WIPO . |
| WO 97/12864 | 4/1997 | WIPO . |

OTHER PUBLICATIONS

"Palladium–Catalyzed Carbonylation of Benzyl Alcohol and Its Analogs Promoted by HI in Aqueous Systems," Y. Lin and A. Yamamoto, Tetrahedron Letters, 1997, vol. 38, No. 21, pp. 3747–3750.

"Synthesis of Lactones by the Palladium–Catalyzed Carbonylation of Halo Alcohols," A. Cowell and J.K. Stille , J. Am.Chem.Soc. 1980, vol. 102, pp. 4193–4198.

Hollemann–Wiberg,Lehrbuch Der Anorganischen Chemie, 91–100 Edition, Verlag Walter de Gruyter, Berlin 1985, pp. 246–248.

"The Acidity Scale of HCl Solutions in N,N–Dimethylformamide," I.S. Kislina, S.G. Sysoeva, & O.N. Temkin, Russian Chemical Bulletin, vol. 43, No. 6, Jun. 1994, pp. 960–960.

*Primary Examiner*—Amelia Owens
*Attorney, Agent, or Firm*—Scott E. Hanf

[57]   ABSTRACT

The present invention relates to a process for preparing an isochroman-3-one of the formula (I)

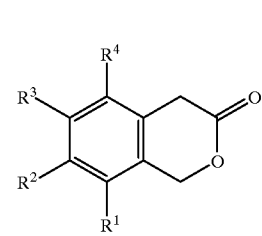

(I)

by reacting a 1,2-bishalomethylbenzene of the formula (II)

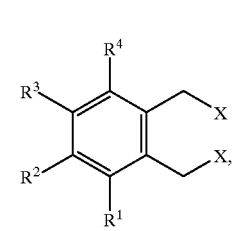

(II)

in which X is chlorine, bromine or iodine with carbon monoxide and water at a CO pressure of from 0.1 to 50 MPa and a temperature of from 20 to 200° C. in the presence or absence of an ionic halide, in the presence of a palladium catalyst and a dipolar aprotic solvent, where in the formulae (I) and (II) the radicals $R^1$, $R^2$, $R^3$ and $R^4$ independently of one another denote:

a hydrogen or fluorine atom;

a $HO_2CCH=CH-$, $NC-$ or $F_3C$ group;

an alkyl, alkoxy or acyloxy radical having in each case 1 to 18 carbon atoms; or a $C_6-C_{18}$-aryloxy, aryl or heteroaryl radical, where the heteroatoms present are 1 to 3 atoms from the group O, N and/or S;

a $R^5{}_2P(=O)-$, $R^6C(=O)-$, $R^6OC(=O)-$, $R^6OC(=O)CH=CH-$, $R^7C(=O)-$, $R^7OC(=O)CH=CH-$ or $R^7{}_2P(=O)$ radical; in which $R^5$ is a $C_1-C_4$-alkyl radical, $R^6$ is a $C_1-C_{18}$-alkyl radical and $R^7$ is a $C_6-C_{18}$-aryl radical; or in which at least one of the radicals $R^1$, $R^2$, $R^3$ and $R^4$ is substituted by a radical $R^8$, where $R^8$ has the same meaning as $R^1$; or where at least two of the radicals $R^1$, $R^2$, $R^3$ and $R^4$ are linked with one another and form at least one aliphatic or aromatic ring having 5 to 18 carbon atoms.

17 Claims, No Drawings

PROCESS FOR PREPARING ISOCHROMAN-3-ONES

CROSS-REFERENCE TO RELATED APPLICATION

The present invention is described in the German priority application No. DE 198 15 323.6, filed Apr. 6, 1998, which is hereby incorporated by reference as is fully disclosed herein.

BACKGROUND OF THE INVENTION

The present invention relates to an advantageous process for preparing isochroman-3-ones.

Isochroman-3-one is of great interest as an intermediate in the synthesis of pharmaceuticals and crop protection agents.

WO 97/12864, for example discloses the use of isochroman-3-one as an intermediate in the preparation of fungicides and pesticides.

The quality of traditional chemical processes is usually defined by the space/time yield. In contrast, in catalytical chemical processes the catalytical turnover number ("TON", i.e. the value which states how frequently a catalyst particle is used in the reaction) and the catalytical turnover frequence ("TOF", i.e. the value which states how frequently a catalyst particle is used in one hour of the reaction) are usually employed as quality criteria. Compared with the space/time yield, TON and TOF give additional information over the quality of the catalyst employed in the reaction.

Various processes for preparing isochroman-3-one are known from the literature. Thus, Yamamoto describes, in Tetrahedron Lett. 1997, Vol. 38, 3747 to 3750, a synthesis of isochroman-3-one by reacting 1,2-bishydroxymethyl-benzene and carbon monoxide in the presence of 1 mol % of a palladium catalyst and 10 mol % of hydrogen iodide. At 90° C. and a carbon monoxide pressure of 9 MPa in acetone/water as solvent, isochroman-3-one is isolated in a yield of 56% after a reaction time of 42 hours.

Disadvantages of this process which may be mentioned are the presence of the highly corrosive hydrogen iodide and the relatively long reaction time.

In J. Am. Chem. Soc. 1980, Vol. 102, 4193 to 4198, Stille describes the synthesis of isochroman-3-one by reaction of ortho-bromomethylbenzyl alcohol, carbon monoxide and potassium carbonate in the presence of 1.6 mol % of a palladium catalyst and a drop of hydrazine in tetrahydrofuran as solvent. After 24 hours at 25° C. and a carbon monoxide pressure of 0.1 MPa, isochroman-3-one is isolated in a yield of 71%.

It is a disadvantage that the ortho-bromomethylbenzyl alcohol, which is required as starting material, is not easily obtainable. In addition, the use of potassium carbonate impedes a simple practice of the process (release of $CO_2$). Furthermore, a relatively long reaction time has to be taken into account.

WO 97/00850 A1 discloses a two-step process for preparing isochroman-3-one derivatives where initially a 1,2-bishalomethylbenzene derivative of the general formula (A)

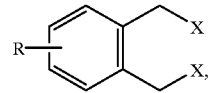

in which R is H, a halogen, a $C_1$–$C_6$-alkyl or a $C_1$–$C_6$-alkoxy radical and X is halogen, carbon monoxide and water are reacted in the presence of a hydrogen halide binder and a catalyst in an organic solvent, and the intermediate salt of the ortho-hydroxymethylphenylacetic acid of the general formula (B) in which M is an alkali metal or alkaline earth metal and n is 1 or 2

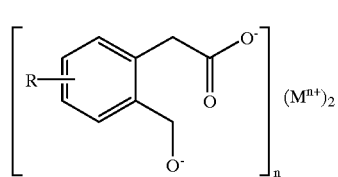

is subsequently treated with an acid and converted into the corresponding isochroman-3-one. Suitable catalysts are palladium, cobalt and iron catalysts. Suitable hydrogen halide binders are bases, in particular inorganic bases, for example calcium hydroxide. The acid used in the second reaction step of this process to bring about conversion of the salt of the ortho-hydroxymethylphenylacetic acid derivatives of the formula (B) into the corresponding isochroman-3-one is, for example, hydrochloric acid. The maximum TOF is $153 \times h^{-1}$; TON=153; yield 76.7% (cf. working example 4). The maximum TON is 170 (TOF=$24 \times h^{-1}$); yield 84.7% (cf. working example 17).

According to this process, it is possible to obtain a yield of up to 87.4% of isochroman-3-one, but a relatively small amount of 8.75 g of α,α'-ortho-xylylene dichloride (1,2-bischloromethylbenzene) is reacted in not less than 100 g of tertbutanol. For further work-up, the reaction mixture is admixed with water, insoluble solids are separated off by filtration and the mixture is repeatedly extracted with ether. After acidification with concentrated hydrochloric acid, the mixture is once more extracted with ether, and isochroman-3-one is obtained from the collected ether fractions (TON= 87; TOF=$4.2 \times h^{-1}$; cf. also working example 5).

Owing to bases being used in the first step of the process and acidification in the second step, not less than 3 equivalents of monovalent salt are formed per equivalent of isochroman-3-one. Disadvantages of this process are, on the one hand, the use of large amounts of solvent and the formation of great amounts of salt and, on the other hand, the fact that it is a two-step process, and the numerous purification and extraction steps and the repeated use of ether as extractant.

SUMMARY OF THE INVENTION

With a view to the disadvantages of the processes illustrated above, it is the object of the present invention to provide a novel process for preparing isochroman-3-ones which, on the one hand, can be carried out with comparably low expense and which, on the other hand, does not have the above-described disadvantages of the processes of the prior art and affords the desired product in good yield and high purity.

DESCRIPTION OF THE PREFERRED EMBODIMENTS

This object is achieved by a process for preparing an isochroman-3-one of the formula (I)

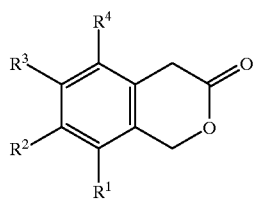

(I)

by reacting a 1,2-bishalomethylbenzene of the formula (II)

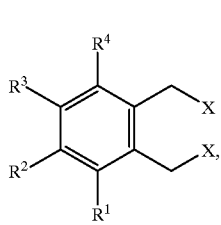

(II)

in which X is chlorine, bromine or iodine with carbon monoxide and water at a CO pressure of from 0.1 to 50 MPa and a temperature of from 20 to 200° C. in the presence or absence of an ionic halide, in the presence of a palladium catalyst and a dipolar aprotic solvent, where in the formulae (I) and (II) the radicals $R^1$, $R^2$, $R^3$ and $R^4$ independently of one another denote:

a hydrogen or fluorine atom;

a $HO_2CCH=CH-$, $NC-$ or $F_3C$ group;

an alkyl, alkoxy or acyloxy radical having in each case 1 to 18 carbon atoms; or a $C_6-C_{18}$-aryloxy, aryl or heteroaryl radical, where the heteroatoms present are 1 to 3 atoms from the group O, N and/or S;

a $R^5_2P(=O)-$, $R^6C(=O)-$, $R^6OC(=O)-$, $R^6OC(=O)CH=CH-$, $R^7C(=O)-$, $R^7OC(=O)CH=CH-$ or $R^7_2P(=O)$ radical; in which $R^5$ is a $C_1-C_4$-alkyl radical, $R^6$ is a $C_1-C_{18}$-alkyl radical and $R^7$ is a $C_6-C_{18}$-aryl radical; or in which at least one of the radicals $R^1$, $R^2$, $R^3$ and $R^4$ is substituted by a radical $R^8$, where $R^8$ has the same meaning as $R^1$; or where at least two of the radicals $R^1$, $R^2$, $R^3$ and $R^4$ are linked with one another and form at least one aliphatic or aromatic ring having 5 to 18 carbon atoms.

Using the process according to the invention, it is possible to react 1,2-bis-halo-methylbenzene of the formula (II) at concentrations which are significantly higher than those of the process according to WO 97/00850 A1. Thus, the space/time yield is increased in an advantageous manner and an industrial realization becomes more favorable to a corresponding degree.

A further advantage consists in the fact that, in contrast to the process of WO 97/00850 A1, it is not necessary to form the salt of the formula (B), and the second reaction step with addition of acid can be dispensed with.

The radicals $R^1$, $R^2$, $R^3$ and $R^4$ independently of one another are in particular hydrogen, fluorine, $C_1-C_4$-alkyl or $C_1-C_4$-alkoxy, or two of the radicals $R^1$, $R^2$, $R^3$ and $R^4$ are linked with one another and form an aliphatic or aromatic ring having 5 to 10 carbon atoms. Preferably, $R^1$, $R^2$, $R^3$ and $R^4$ independently of one another are hydrogen, fluorine or $C_1-C_4$-alkyl.

In the formulae (I) and (II), two, three or four, in particular three or four, of the radicals $R^1$, $R^2$, $R^3$ and $R^4$ are hydrogen.

With good results, a 1,2-bishalomethylbenzene of the formula (II) in which X is chlorine or bromine, in particular chlorine, can be employed for the process.

As mentioned at the outset, the process can be carried out in the presence or absence of an ionic halide.

The ionic halide is usually an alkali metal halide, ammonium halide or phosphonium halide, in particular an alkali metal halide or ammonium halide, where halide is chloride, bromide or iodide, in particular chloride or bromide, preferably chloride.

The ionic halide used can be ammonium bromide, lithium bromide, sodium bromide, potassium bromide, tetrabutylphosphonium bromide, ammonium chloride, dimethylammonium chloride, diethanolammonium chloride, lithium chloride, sodium chloride, potassium chloride, tetrabutylphosphonium chloride, ammonium iodide, lithium iodide, sodium iodide, potassium iodide and/or tetrabutylphosphonium iodide, in particular lithium chloride, ammonium chloride, dimethylammonium chloride and/or diethanolammonium chloride.

It may be mentioned here that it is not necessary for the ionic halide to be present, and that the process can be carried out, in particular, in the absence of the ionic halide.

A palladium catalyst comprising palladium applied to a support can be used for the process. Such a supported palladium catalyst has the advantage that it can be removed in a simple manner from the reaction mixture, for example by filtration.

In a number of cases it has proved useful for the palladium catalyst to comprise at least one palladium(II) compound, in particular $PdCl_2$, $PdBr_2$ or $Pd(OAc)_2$, preferably $PdCl_2$, or at least one palladium(O) compound, in particular $Pd_2dba_3$, where dba is dibenzylideneacetone, $Pd(P(C_6H_5)_3)_4$ or $Pd(\eta^4-C_8H_{12})_2$, preferably $Pd_2dba_3$.

In a number of cases it has furthermore proved useful for the palladium catalyst additionally to comprise a ligand, in particular a phosphine compound.

Suitable phosphine compounds are, for example, a monophosphine, in particular a tri($C_1-C_6$-alkyl)phosphine or a triarylphosphine, or a diphosphine. Triphenylphosphine, tritolylphosphine, bis(diphenylphosphino)ethane, 1,3-bis (diphenylphosphino)propane or 1,4-bis(diphenylphosphino) butane, in particular triphenylphosphine, can be employed with good success.

According to a particular embodiment, the palladium catalyst comprises a bis(triphenylphosphine)palladium(II) compound, for example bis(triphenylphosphine)palladium (II) chloride or bis(triphenylphosphine)-palladium(II) bromide.

The palladium catalyst is usually employed in an amount corresponding to from 0.00001 to 0.3 mol of palladium, in particular from 0.000025 to 0.2 mol of palladium, preferably from 0.00005 to 0.1 mol of palladium per mole of 1,2-bishalomethylbenzene.

In a large number of cases it is sufficient to carry out the reaction at a CO pressure of from 0.5 to 20 MPa, in particular from 0.8 to 10, preferably from 1.0 to 6, MPa.

The reaction can usually be carried out with good success at a temperature of from 50 to 170° C., in particular from 70 to 160° C., preferably from 90 to 150° C.

Suitable dipolar aprotic solvents are dioxane, tetrahydrofuran, an N-($C_1-C_{18}$-alkyl)pyrrolidone, ethylene glycol dimethyl ether, a $C_1-C_4$-alkyl ester of an aliphatic $C_1-C_6$-carboxylic acid, a $C_1-C_6$-dialkyl ether, an N,N-di- ($C_1-C_4$-alkyl)amide of an aliphatic $C_1-C_4$-carboxylic acid, sulfolane, a 1,3-di-($C_1-C_8$-alkyl)-2-imidazolidinone, an N-($C_1-C_8$-alkyl)caprolactam, an N,N,N',N'-tetra-($C_1-C_8$- alkyl)urea, a 1,3-di-($C_1$–$C_8$-alkyl)-3,4,5,6-tetrahydro-2 (1H)-pyrimidone, an N,N,N',N'-tetra-($C_1$–$C_8$-alkyl) sulfamide, 4-formylmorpholine, 1-formylpiperidine or 1-formylpyrrolidine, in particular an N-($C_1$–$C_{18}$-alkyl) pyrrolidone, an N,N-di-($C_1$–$C_4$-alkyl)amide of an aliphatic $C_1$–$C_4$-carboxylic acid, 4-formylmorpholine, 1-formylpiperidine or 1-formylpyrrolidine, preferably N-methylpyrrolidone, N-octylpyrrolidone, N-dodecylpyrrolidone, N,N-dimethylformamide, N,N-dimethylacetamide, 4-formylmorpholine, 1-formylpiperidine or 1-formylpyrrolidine, particularly preferably N-methylpyrrolidone, N,N-dimethylformamide or N,N-dimethylacetamide, very particularly preferably N-methylpyrrolidone. It is also possible to use mixtures of the abovementioned dipolar aprotic solvents.

Water can be employed in the process in an amount corresponding to from 0.5 to 50 mol per mole of 1,2-bishalomethylbenzene of the formula (II). Usually, the reaction is carried out with an amount of water corresponding to from 1 to 10, in particular from 1 to 4, preferably from 1 to 3, mol of water per mole of 1,2-bishalomethylbenzene of the formula (II).

According to a particular embodiment of the process according to the invention, the 1,2-bishalomethylbenzene of the formula (II), the palladium catalyst, the dipolar aprotic solvent and, if appropriate, the ionic halide are initially charged, the CO pressure and the temperature are set and water or a mixture comprising water and dipolar aprotic solvent is subsequently metered in.

During the reaction, the reactants are mixed well to ensure a speedy progress of the reaction.

The process according to the invention is suitable both for continuous and batchwise practice.

The reaction is usually carried out at a $H_0$ value $\leq 7$, in particular at $H_0 = -3$ to 7, preferably at $-2$ to 6. However, it is also possible to carry out the reaction at an $H_0$ value of from $-1$ to 5, in particular from $-1$ to 4. The $H_0$ value, which is a measure for the acidity of a solvent and for which $H_0 \approx pH$ applies to dilute solutions is described in Hollemann-Wiberg "Lehrbuch der Anorganischen Chemie", 91–100. Edition, Verlag Walter de Gruyter, Berlin 1985, on pages 246–248. Kislina et al. describe, for example, the acidity of HCl in N,N-dimethylformamide in Russ. Chem. Bull., 1994, Vol. 43, on pages 960–963. The corresponding $H_0$ value usually establishes itself in the course of a reaction, so that additional measures for setting the $H_0$ value are usually not required.

The $H_0$ value is defined by the following equation: $H_0 = pK_{S,In} + \log C_{In}/C_{InH}^+$ (Hammett acidity function). Here, In denotes the indicator base and $InH^+$ denotes the protonated form of the indicator base.

The examples below illustrate the invention without limiting it.

EXAMPLES

Experimental Part

Example 1

Preparation of isochroman-3-one 700 g of 1,2-bischloromethylbenzene, 2.8 g of bis(triphenylphosphine)-palladium(II) chloride and 2.4 g of triphenylphosphine are dissolved in 1000 ml of dimethylformamide and mixed in a 3000 ml autoclave of HC 4 steel under an atmosphere of protective gas (argon). Carbon monoxide is subsequently added at a pressure of 3 MPa, and the temperature is increased to 130° C.

At 130° C. and a pressure of 4 MPa, 400 ml of a mixture of water/dimethylformamide (ratio by weight 2.5:1.5) are metered in over a period of 2 hours. During the addition, the reaction pressure is maintained at a constant 4 MPa. After the addition, the mixture is allowed to react with stirring for another hour and then cooled to 90° C., and the autoclave is emptied.

This gives 2065 g of reaction mixture. Gas chromatographic analysis shows that the reaction mixture contains 408 g of isochroman-3-one, corresponding to a yield of 70% of isochroman-3-one, based on the 1,2-bischloromethylbenzene employed (TON=700; TOF=255× $h^{-1}$).

From the reaction mixture, 733 g of low-boiling components are separated off in a thin-layer evaporator at 100° C. and 10 mbar.

The isochroman-3-one-containing residue is admixed with water. Isochroman-3-one of a purity of about 90% ($^1$H NMR analysis) precipitates out. By distillation, 281 g of isochroman-3-one of melting point 79–80° C. (purity 97%) are obtained.

$^1$H NMR (300 MHz $CDCl_3$): $\delta$=7.20 to 7.40 (m, 4H), 5.31 (s, 2H), 3.71 (s, 2H).

Example 2

Preparation of isochroman-3-one 52.5 g of 1,2-bischloromethylbenzene, 10.8 g of water, 0.21 g of bis(triphenyl-phosphine)palladium(II) chloride and 0.18 g of triphenylphosphine are dissolved in 100 ml of N-methylpyrrolidone and mixed in a 200 ml autoclave of HC 4 steel under an atmosphere of protective gas (argon).

Carbon monoxide is subsequently added at a pressure of 3 MPa, and the temperature is increased to 130° C. During the reaction, the reaction pressure is maintained between 3.5 and 4.0 MPa. After a reaction time of 3 hours, the mixture is stirred for another hour and cooled to 90° C., and the autoclave is emptied.

This gives 150 g of reaction mixture. Gas chromatographic analysis shows that the reaction mixture contains 20.4 g of isochroman-3-one (yield 46%; TON=460; TOF= 153 $h^{-1}$).

Comparative Example 1

52.5 g of 1,2-bischloromethylbenzene, 1.05 g of bis(triphenylphosphine)-palladium(II) chloride and 0.87 g of triphenylphosphine are mixed in 100 ml of tertbutanol and, in a 500 ml glass autoclave and under an atmosphere of protective gas (argon), suspended in 48.0 g of water and 46.8 g of calcium hydroxide.

Under an atmosphere of carbon monoxide, the temperature is subsequently increased to 70° C. Carbon monoxide uptake, started with vigorous stirring at 60° C., ceases after 2 hours, and a viscous pulp is obtained. Addition of a further 1.05 g of bis(triphenylphosphine)-palladium(II) chloride and 0.87 g of triphenylphosphine does not lead to any further uptake of carbon monoxide.

After cooling, the mixture is acidified to pH 1 using hydrochloric acid and extracted with diethyl ether. This gives 383 g of an aqueous phase and 299 g of an organic phase. According to gas chromatographic analysis, the aqueous phase does not contain any isochroman-3-one, and the organic phase, according to gas chromatographic analysis, contains 10.5 g of isochroman-3-one (yield 24%; TON=46; TOF=15.4×$h^{-1}$).

Example 3

35.0 g of 1,2-bischloromethylbenzene, 140 mg of bis(triphenylphosphine)-palladium(II) chloride and 120 mg of triphenylphosphine are dissolved in 80 ml of N-methylpyrrolidone and mixed in a 200 ml autoclave of HC 4 steel under an atmosphere of protective gas (argon).

Carbon monoxide is subsequently added at a pressure of 3.0 MPa, and the temperature is increased to 130° C. At 130° C. and a pressure of from 3.5 MPa to 4.0 MPa, 32.5 ml of water/N-methylpyrrolidone (ratio by weight 1:5) are metered in over a period of 3 hours. After the addition, the mixture is cooled to 75° C. and the autoclave is vented.

This gives 162 g of reaction mixture. Gas chromatographic analysis shows that the reaction mixture contains 17.2 g of isochroman-3-one (yield 58%; TON=584; TOF=195×h$^{-1}$).

Comparative Example 2

Preparation of isochroman-3-one using pyridine as hydrogen halide binder.

Example 3 is repeated, but instead of 80 ml of the dipolar aprotic solvent N-methylpyrrolidone, 80 ml of pyridine are used as hydrogen halide binder and solvent.

This gives 152 g of a two-phase reaction mixture. Gas chromatographic analysis shows that neither of the two phases contains isochroman-3-one. In spite of the presence of a hydrogen halide binder, no isochroman-3-one has been formed.

Example 4

20.5 g of 1,2-bischloromethylbenzene, 70 mg of bis(triphenylphosphine)-palladium(II) chloride and 60 mg of triphenylphosphine are dissolved in 50 ml of N,N-dimethylformamide and mixed in a 200 ml autoclave of HC 4 steel under an atmosphere of protective gas (argon).

Carbon monoxide is subsequently added at a pressure of 1.7 MPa, and the temperature is increased to 130° C. At 130° C. and a pressure of 2.3 MPa, 15 ml of water/dimethylformamide (ratio by weight 1:4) are metered in over a period of 5 hours. After the addition, the mixture is stirred for another hour and the autoclave is vented. 15 ml of water are subsequently added, and the mixture is allowed to cool to room temperature whilst being stirred.

This gives 95.8 g of reaction mixture. Gas chromatographic analysis shows that the reaction mixture contains 13 g of isochroman-3-one (which corresponds to a yield of 75%, TON=900; TOF=180×h$^{-1}$).

Example 5

87.2 g of 1,2-bischloromethylbenzene, 175 mg of bis(triphenylphosphine)-palladium(II) chloride and 150 mg of triphenylphosphine are dissolved in 79.8 g of N,N-dimethylformamide and mixed in a 300 ml autoclave of HC 4 steel under an atmosphere of protective gas (argon).

Carbon monoxide is subsequently added at a pressure of 3.0 MPa, and the temperature is increased to 130° C. At 130° C. and a pressure of from 3.5 to 4.0 MPa, 53 ml of water/N,N-dimethylformamide (ratio by weight 1:1) are metered in over a period of 5.6 hours. After the addition, the mixture is cooled and the autoclave is vented.

This gives 222 g of reaction mixture. Gas chromatographic analysis after addition of 15 g of water shows that the reaction mixture contains 36.1 g of isochroman-3-one (yield: 49%; TON=982; TOF=175×h$^{-1}$).

Example 6

35.0 g of 1,2-bischloromethylbenzene and 35 mg of palladium(II) chloride are dissolved in 103 g of N-methylpyrrolidone and mixed in a 200 ml autoclave of HC 4 steel under an atmosphere of protective gas (argon).

Carbon monoxide is subsequently added at a pressure of 16.0 MPa, and the temperature is increased to 150° C. At 150° C. and a pressure of from 1.8 MPa to 2.2 MPa, 7.2 ml of water/N-methylpyrrolidone (ratio by weight 1:1) are metered in over a period of 230 minutes. The experiment is subsequently terminated by venting and cooling the mixture to 50° C. over a period of 15 minutes.

This gives 150 g of reaction mixture. Gas chromatographic analysis shows that the reaction mixture contains 11.4 g of 1,2-bischloromethylbenzene and 14.9 g of isochroman-3-one (selectivity 75%; conversion 67%; TON=503; TOF=131×h$^{-1}$).

Example 7

35.0 g of 1,2-bischloromethylbenzene, 35 mg of palladium(II) chloride and 100 mg of octyltrimethylammonium chloride are dissolved in 103 g of N-methylpyrrolidone and mixed in a 200 ml autoclave of HC 4 steel under an atmosphere of protective gas (argon).

Carbon monoxide is subsequently added at a pressure of 16.0 MPa, and the temperature is increased to 150° C. At 150° C. and a pressure of from 1.8 MPa to 2.2 MPa, 7.2 ml of water/N-methylpyrrolidone (ratio by weight 1:1) are subsequently metered in over a period of 230 minutes. The experiment is subsequently terminated by venting and cooling the mixture to 50° C. over a period of 15 minutes.

This gives 149 g of reaction mixture. Gas chromatographic analysis shows that the reaction mixture contains 15.1 g of 1,2-bischloromethylbenzene and 13.5 g of isochroman-3-one (selectivity 80%; conversion 57%; TON=456; TOF=119×h$^{-1}$).

Example 8

Preparation of isochroman-3-one 299 g of 1,2-bischloromethylbenzene and 75 mg of palladium(II) chloride are dissolved in 880 g of N-methylpyrrolidone and mixed in a 2000 ml autoclave of HC 4 steel under an atmosphere of protective gas (argon). Carbon monoxide is subsequently added at a pressure of 1.5 MPa, and the temperature is increased to 150° C. At 150° C. and a pressure of 2 MPa, 123 g of a mixture of water/N-methylpyrrolidone (ratio by weight 1:1) are metered in over a period of 140 minutes. During the addition, the reaction pressure is maintained at a constant 2 MPa. After the addition, the mixture is allowed to react for a further 20 minutes with stirring, the pressure is slowly released and the autoclave is flushed with nitrogen. The autoclave is subsequently cooled to room temperature and emptied.

This gives 1301 g of reaction mixture. HPLC analysis shows that the reaction mixture contains 164 g of isochroman-3-one, corresponding to a yield of 65% of isochroman-3-one, based on 1,2-bischloromethylbenzene employed (TON=4466; TOF=1675×h$^{-1}$).

Example 9

Continuous preparation of isochroman-3-one 299 g of 1,2-bischloromethylbenzene and 75 mg of palladium(II) chloride are dissolved in 880 g of N-methylpyrrolidone and mixed in a 2000 ml autoclave of HC 4 steel under an atmosphere of protective gas (argon). Carbon monoxide is subsequently added at a pressure of 1.5 MPa, and the temperature is increased to 150° C. At 150° C. and a pressure of 2 MPa, 45.5 g of a mixture of water/N-methyl-pyrrolidone (ratio by weight 1:1) are subsequently metered in over a period of 60 minutes. In the following 30 minutes, a further 4 g of the mixture of water/N-methylpyrrolidone (ratio by weight 1:1) are metered in. Gas chromatographic analysis of a sample shows that the reaction mixture contains 7.5% by weight of 3-isochromanone and 13.3% by weight of 1,2-bischloromethylbenzene. A mixture comprising 24.1% by weight of 1,2-bischloromethylbenzene, 0.0060% by weight of palladium (II) chloride and 2.46% by weight of water in N-methylpyrrolidone is subsequently metered in continuously at a rate of 360 g×h$^{-1}$, and 360 g×h$^{-1}$ of the reaction mixture are simultaneously discharged from the autoclave. Gas chromatographic analysis of a sample of the reaction mixture after a further hour—after 360 g of the reaction mixture have been removed—shows that it contains 7.2% by weight of 3-isochromanone and 13.4% by weight of 1,2-bischloromethylbenzene (for the first hour of continuous operation: TON=1410; TOF=1410×h$^{-1}$). Continuous addition and discharge is subsequently terminated, and the autoclave is vented and cooled to room temperature. During the entire reaction time, the reaction pressure is maintained at a constant 2 MPa.

What is claimed is:

1. A process for preparing a isochroman-3-one of the formula (I)

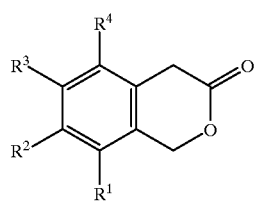

(I)

by reacting a 1,2-bishalomethylbenzene of the formula (II)

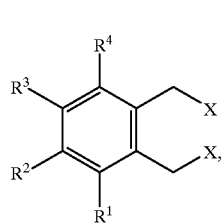

(II)

in which X is chlorine, bromine or iodine with carbon monoxide and water at a CO pressure of from 0.1 to 50 MPa and a temperature of from 20 to 200° C. in the presence or absence of an ionic halide, in the presence of a palladium catalyst and a dipolar aprotic solvent, where in the formulae (I) and (II) the radicals $R^1$, $R^2$, $R^3$ and $R^4$ independently of one another denote:

a hydrogen or fluorine atom;

a $HO_2CCH=CH-$, NC— or $F_3C$ group;

an alkyl, alkoxy or acyloxy radical having in each case 1 to 18 carbon atoms; or a $C_6$–$C_{18}$-aryloxy, aryl or heteroaryl radical, where the heteroatoms present are 1 to 3 atoms from the group O, N and/or S;

a $R^5{}_2P(=O)-$, $R^6C(=O)-$, $R^6OC(=O)-$, $R^6OC(=O)CH=CH-$, $R^7C(=O)-$, $R^7OC(=O)CH=CH-$ or $R^7{}_2P(=O)$ radical; in which $R^5$ is a $C_1$–$C_4$-alkyl radical, $R^6$ is a $C_1$–$C_{18}$-alkyl radical and $R^7$ is a $C_6$–$C_{18}$-aryl radical; or in which at least one of the radicals $R^1$, $R^2$, $R^3$ and $R^4$ is substituted by a radical $R^8$, where $R^8$ has the same meaning as $R^1$; or where at least two of the radicals $R^1$, $R^2$, $R^3$ and $R^4$ are linked with one another and form at least one aliphatic or aromatic ring having 5 to 18 carbon atoms.

2. The process as claimed in claim 1, wherein the radicals $R^1$, $R^2$, $R^3$ and $R^4$ independently of one another are hydrogen, fluorine, $C_1$–$C_4$-alkyl or $C_1$–$C_4$-alkoxy, or two of the radicals $R^1$, $R^2$, $R^3$ and $R^4$ are linked with one another and form an aliphatic or aromatic ring having 5 to 10 carbon atoms.

3. The process as claimed in claim 1, wherein two, three or four of the radicals $R^1$, $R^2$, $R^3$ and $R^4$ are hydrogen.

4. The process as claimed in claim 1, wherein the ionic halide is an alkali metal halide, ammonium halide or phosphonium halide, where halide is chloride, bromide or iodide.

5. The process as claimed in claim 1, wherein the ionic halide is ammonium bromide, lithium bromide, sodium bromide, potassium bromide, tetrabutylphosphonium bromide, ammonium chloride, dimethylammonium chloride, diethanolammonium chloride, lithium chloride, sodium chloride, potassium chloride, tetrabutylphosphonium chloride, ammonium iodide, lithium iodide, sodium iodide, potassium iodide and/or tetrabutylphosphonium iodide.

6. The process as claimed in claim 1, wherein the palladium catalyst comprises metallic palladium applied to a support.

7. The process as claimed in claim 1, wherein the palladium catalyst comprises at least one palladium(II) compound, in particular $PdCl_2$, $PdBr_2$ or $Pd(OAc)_2$, or at least one palladium(O) compound, in particular $Pd_2dba_3$, $Pd(P(C_6H_5)_3)_4$ or $Pd(\eta^4\!\!-\!\!C_8H_{12})_2$.

8. The process as claimed in claim 7, wherein the palladium catalyst additionally comprises a ligand, in particular a phosphine compound.

9. The process as claimed in claim 8, wherein the phosphine compound is triphenylphosphine, tritolylphosphine, bis(diphenylphosphino)ethane, 1,3-bis(diphenylphosphino)propane or 1,4-bis(diphenylphosphino)butane.

10. The process as claimed in claim 1, wherein the palladium catalyst comprises bis(triphenylphosphine)palladium(II) chloride or bis(triphenylphosphine)palladium(II) bromide.

11. The process as claimed in claim 1, wherein the palladium catalyst is employed in an amount corresponding to from 0.00001 to 0.3 mol of palladium per mole of 1,2-bishalomethylbenzene.

12. The process as claimed in claim 1, wherein the reaction is carried out at a CO pressure of from 0.5 to 20 MPa.

13. The process as claimed in claim 1, wherein the reaction is carried out at a temperature of from 50 to 170° C.

14. The process as claimed in claim 1, wherein the dipolar aprotic solvent is dioxane, tetrahydrofuran, an N-($C_1$–$C_{18}$-alkyl)pyrrolidone, ethylene glycol dimethyl ether, a $C_1$–$C_4$-alkyl ester of an aliphatic $C_1$–$C_6$-carboxylic acid, a $C_1$–$C_6$-dialkyl ether, an N,N-di-($C_1$–$C_4$-alkyl)amide of an aliphatic $C_1$–$C_4$-carboxylic acid, sulfolane, 1,3-di-($C_1$–$C_8$-alkyl)-2-imidazolidinone, an N-($C_1$–$C_8$-alkyl)caprolactam, an N,N,N',N'-tetra-($C_1$–$C_8$-alkyl)urea, a 1,3-di-($C_1$–$C_8$-alkyl)-3,4,5,6-tetrahydro-2(1H)-pyrimidone, an N,N,N',N'-tetra-($C_1$–$C_8$-alkyl)sulfamide, 4-formylmorpholine, 1-formylpiperidine or 1-formylpyrrolidine.

15. A process as claimed in claim 1, wherein the dipolar aprotic solvent is N-methylpyrrolidone, N-octylpyrrolidone, N-dodecylpyrrolidone, N,N-dimethylformamide, N,N-dimethylacetamide, 4-formylmorpholine, 1-formylpiperidine or 1-formylpyrrolidine.

16. The process as claimed in claim 1, wherein water is employed in an amount corresponding to from 1 to 10 mol per mol of 1,2-bishalomethylbenzene of the formula (II).

17. The process as claimed in claim 1, wherein the 1,2-bis-halomethylbenzene of the formula (II), the palladium catalyst, the dipolar aprotic solvent and, if appropriate, the ionic halide are initially charged, the CO pressure and the temperature are set and the water or a mixture comprising water and dipolar aprotic solvent is subsequently metered in.

* * * * *